(12) United States Patent
Wuttke et al.

(10) Patent No.: US 7,537,006 B2
(45) Date of Patent: May 26, 2009

(54) NEBULIZER

(75) Inventors: Gilbert Wuttke, Dortmund (DE); Hubert Kunze, Dortmund (DE); Ralf Thoemmes, Willich (DE)

(73) Assignee: Boehringer Ingelheim International GmbH, Ingelheim (DE)

( * ) Notice: Subject to any disclaimer, the term of this patent is extended or adjusted under 35 U.S.C. 154(b) by 167 days.

(21) Appl. No.: 11/064,616

(22) Filed: Feb. 24, 2005

(65) Prior Publication Data

US 2005/0183719 A1    Aug. 25, 2005

(30) Foreign Application Priority Data

Feb. 24, 2004    (DE) .................. 10 2004 009 436

(51) Int. Cl.
*A61M 11/00*    (2006.01)
(52) U.S. Cl. ................................. 128/200.14
(58) Field of Classification Search ...............
128/200.14–200.23, 203.16, 203.17, 203.27, 128/205.23; 239/333, 302, 349, 355, 357–363; 222/373, 379, 383.1, 385, 401, 402
See application file for complete search history.

(56) References Cited

U.S. PATENT DOCUMENTS

| | | | |
|---|---|---|---|
| 3,343,797 A * | 9/1967 | Bach .......................... 239/355 |
| 4,017,031 A * | 4/1977 | Kishi et al. .................. 239/333 |
| 4,034,757 A | 7/1977 | Glover |
| 4,277,001 A * | 7/1981 | Nozawa .................... 222/321.4 |
| 4,382,688 A | 5/1983 | Machamer |
| 4,817,822 A | 4/1989 | Rand et al. |
| 5,020,527 A | 6/1991 | Dessertine |
| 5,284,133 A | 2/1994 | Burns et al. |
| 5,507,277 A * | 4/1996 | Rubsamen et al. ..... 128/200.14 |
| 5,664,703 A | 9/1997 | Reifenberger et al. |
| 5,964,416 A * | 10/1999 | Jaeger et al. ................ 239/333 |
| 6,202,642 B1 * | 3/2001 | McKinnon et al. ..... 128/200.23 |
| 6,234,366 B1 | 5/2001 | Fuchs |
| 6,958,691 B1 * | 10/2005 | Anderson et al. ...... 340/539.12 |
| 2003/0192535 A1 | 10/2003 | Christrup et al. |
| 2003/0205229 A1 | 11/2003 | Crockford et al. |

FOREIGN PATENT DOCUMENTS

| | | |
|---|---|---|
| EP | 0 013 534 A1 | 7/1980 |
| EP | 0 014 814 A1 | 9/1980 |
| EP | 0 039 004 A2 | 11/1981 |
| WO | WO 91/14468 A1 | 10/1991 |
| WO | WO 97/12687 A1 | 4/1997 |

* cited by examiner

*Primary Examiner*—Steven O Douglas
(74) *Attorney, Agent, or Firm*—David S. Safran; Roberts Mlotkowski Safran & Cole, P.C.

(57) ABSTRACT

A nebulizer for a fluid having a pressure generator for conveying and nebulizing the fluid, particularly in the form of an inhaler, is proposed. To improve the user guidance it is envisaged that the nebulizer should have a signal device for generating at least one acoustic and/or vibratory signal, particularly during a nebulizing process.

35 Claims, 6 Drawing Sheets

NEBULIZER

BACKGROUND OF THE INVENTION

1. Field of the Invention

The present invention relates to a nebulizer according to the preamble of claim 1.

2. Description of the Prior Art

The starting point for the present invention is a nebulizer in the form of an inhaler as shown in principle in WO 91/14468 and specifically in WO 97/12687 (FIGS. 6a, 6b) and in FIGS. 1 and 2 of the enclosed drawings. The nebulizer comprises as a reservoir for a fluid which is to be nebulised an insertable container with the fluid and a pressure generator with a drive spring for conveying and atomising the fluid. WO 91/14468 and WO 97/12687 are hereby incorporated by reference in their entireties. Generally, the disclosures thereof refer to a nebulizer having a spring pressure of 5 to 60 MPa, preferably 10 to 50 Mpa, on the fluid with volumes per actuation of 10 to 50 μl, preferably 10 to 20 μl, most preferably about 15 μl, per actuation and particle sizes of up to 20 μm, preferably 3 to 10 μm. Moreover, the disclosures therein preferably relate to a nebulizer with a cylinder-like shape that is about 9 cm to about 15 cm long and about 2 to about 5 cm wide and a nozzle spray spread of from 20° to 160°, preferably from 80° to 100°. These magnitudes also apply to the nebulizer according to the teaching of the invention as particularly preferred values.

By rotating an actuating member in the form of a lower housing part of the nebulizer the drive spring can be put under tension and fluid can be drawn up into a pressure chamber of the pressure generator. After manual actuation of a locking element the fluid in the pressure chamber is put under pressure by the drive spring and nebulized, i.e. expelled to form an aerosol. During the tensioning process, on the one hand, and subsequent atomizing, on the other hand, the container performs a lifting movement.

The nebulizer comprises a mechanical monitoring device which detects the rotation of the actuating member in order to count the actuations of the nebulizer. The known nebulizer operates exclusively mechanically, i.e. without propellant gas and without electricity.

SUMMARY OF THE INVENTION

The aim of the present invention is to provide a nebulizer which has better guidance for the user.

This objective is achieved by a nebulizer according to claim 1. Advantageous features are recited in the subsidiary claims.

A fundamental idea of the present invention consists in providing a signal device for generating at least one acoustic and/or vibratory signal for user guidance. This provides better information for the user, even during the inhaling process, in particular, so as to allow better handling and safety in use.

In the present invention the term "vibratory signal" is preferably to be understood in a wider sense as meaning that it includes other tactile signals such as the movement of part of the nebulizer, movement or release of an actuating element or the like.

In particular, the nebulizer comprises a mouthpiece, so that the user puts the mouthpiece in their mouth in order to use the nebulizer. During the nebulizing and inhaling process, any optical display which may be showing on the nebulizer cannot be seen by the user. However, an acoustic and/or vibratory signal can be registered by the user even during the inhalation process.

A particular advantage of a vibratory signal is that when a user is holding a mouthpiece any vibratory signal can be relatively weak, i.e. may have a low amplitude, but will still be very easily perceived by the user.

Alternatively or in addition to the detection of the vibratory signal through a mouthpiece, the nebulizer may also be designed so that the vibratory signal can be perceived by the hand of the user holding the nebulizer, particularly a finger. It may be sufficient if for example only a section or part of the nebulizer, such as an operating button, vibrates or generates some other tactile signal such as a movement.

Another advantage resides in the discreet nature of the arrangement, as the user can detect a vibratory signal without the signal being noticeable to third parties.

According to an alternative embodiment a signal can be produced throughout the nebulizing process and/or at the end of the nebulizing process, to inform the user accordingly.

Alternatively or in addition, starting with a nebulizing process, a signal can be generated throughout a predetermined period of time and/or after this period has elapsed. This signal indicates to a user the ideal or necessary inhalation period, or the time for which a user should hold their breath immediately after inhaling, or the end of this time once it has been correspondingly selected—e.g. 1 to 15 seconds longer than the nebulizing process.

Alternatively or in addition, a signal may be generated throughout an actual inhalation process and/or at the end of an actual inhalation process, while the signal may also depend on the intensity of inhalation and may possibly indicate that inhalation has been sufficiently powerful or not powerful enough. In particular, the nebulizer comprises a sensor in the region of a mouthpiece of the nebulizer, for detecting an air supply current sucked in by the user as they inhale and thereby detecting the inhalation.

Preferably the nebulizer indicates to the user, by means of the signal or different signals, the start, duration and/or end of the nebulizing process, a subsequent (ideal or actual) period of inhalation and/or a desired period of time, preferably from about 5 to 15 seconds, during which a user should hold their breath immediately after inhaling.

According to a particularly preferred alternative feature the signal device like the pressure generator operates exclusively mechanically, i.e. without electricity, propellant gas or the like.

DESCRIPTION OF THE DRAWINGS

Further advantages, features, properties and aspects of the present invention will become apparent from the following description of preferred embodiments referring to the drawings, wherein.

In the Figures, identical reference numerals are used for identical or similar parts, and corresponding or comparable properties and advantages are achieved even if the description is not repeated.

DESCRIPTION OF THE INVENTION

Figure 1:
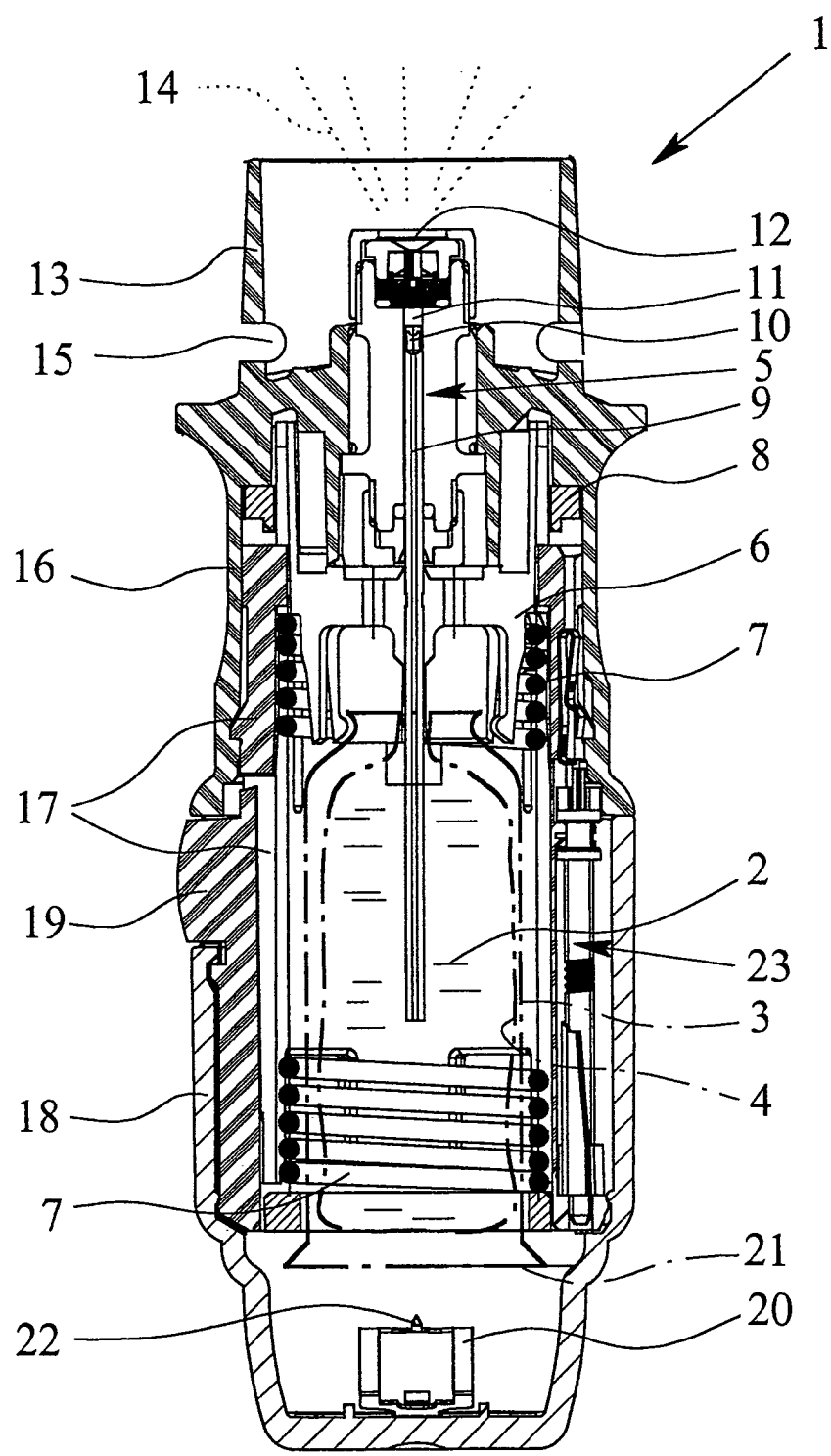
FIG. 1 is a diagrammatic section through a known nebulizer in the untensioned state.
Figure 2:
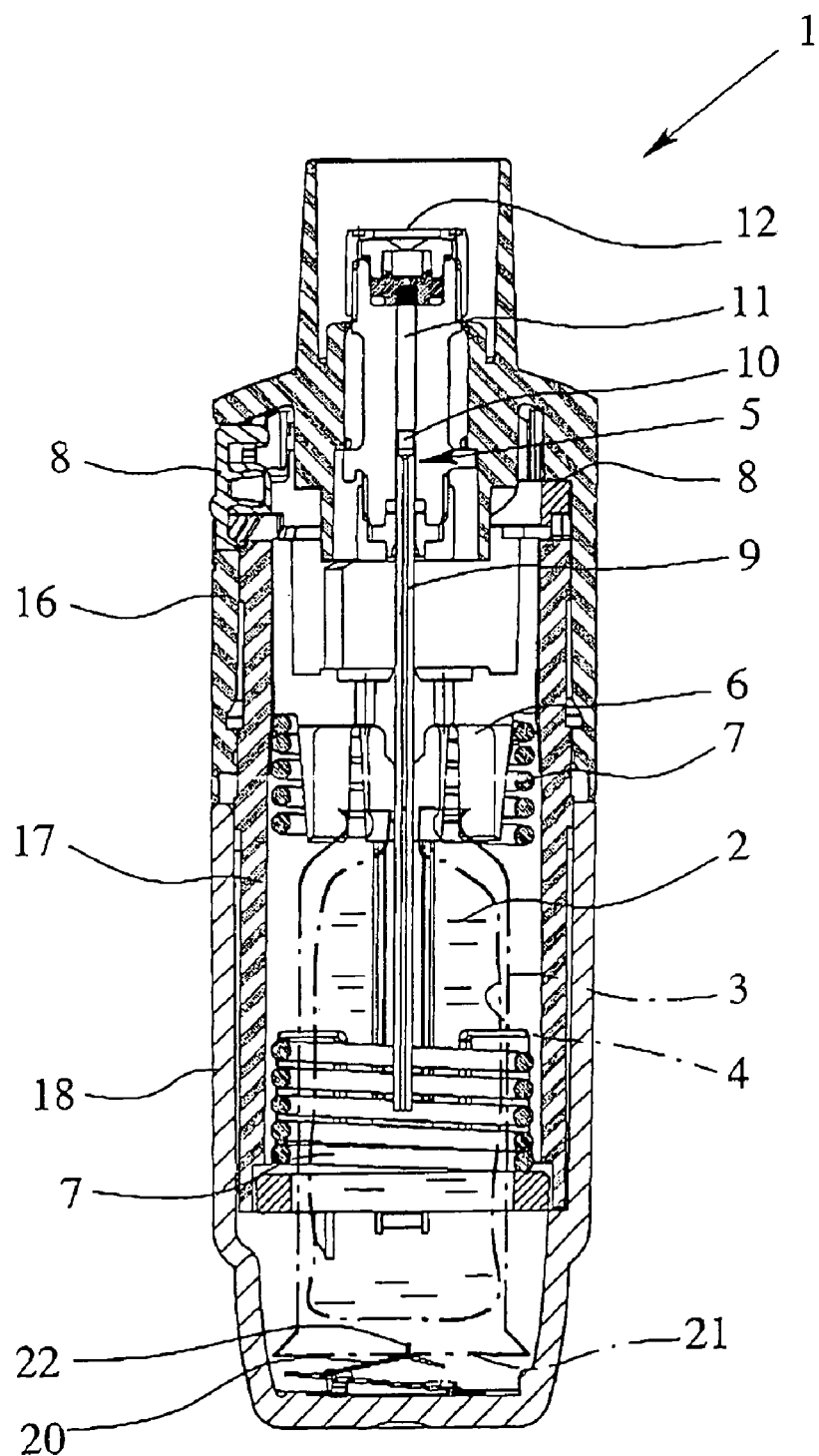
FIG. 2 shows a diagrammatic section through the known atomiser in the tensioned state, rotated through 90° compared with FIG. 1.

FIGS. 1 and 2 show a known nebulizer 1 for nebulizing a fluid 2, particularly a highly effective pharmaceutical composition or the like, viewed diagrammatically in the untensioned state (FIG. 1) and in the tensioned state (FIG. 2). The nebulizer is constructed in particular as a portable inhaler and preferably operates without propellant gas.

When the fluid 2, preferably a liquid, more particularly a pharmaceutical composition, is nebulised, an aerosol is formed which can be breathed in or inhaled by a user. Usually the inhaling is done at least once a day, more particularly several times a day, preferably at set intervals.

The nebulizer 1 has an insertable and preferably exchangeable container 3 containing the fluid 2, which forms a reservoir for the fluid 2 which is to be nebulised. Preferably, the container 3 contains an amount of fluid 2 sufficient for multiple use, particularly for a given period of administration, such as one month, or for at least 50, preferably at least 100, doses or sprays.

The container 3 is substantially cylindrical or cartridge-shaped and once the nebulizer 1 has been opened the container can be inserted therein from below and changed if desired. It is preferably of rigid construction, the fluid 2 in particular being held in a bag 4 in the container 3.

The nebulizer 1 has a pressure generator 5 for conveying and nebulizing the fluid 2, particularly in a preset and optionally adjustable dosage amount. The pressure generator 5 has a holder 6 for the container 3, an associated drive spring 7, only partly shown, with a locking element 8 which can be manually operated to release it, a conveying tube 9 with a non-return valve 10, a pressure chamber 11 and an expulsion nozzle 12 in the region of a mouthpiece 13.

As the drive spring 7 is axially tensioned the holder 6 with the container 3 and the conveying tube 9 is moved downwards in the drawings and fluid 2 is sucked out of the container 3 into the pressure chamber 11 of the pressure generator 5 through the non-return valve 10. As the expulsion nozzle 12 has a very small cross section of flow and is constructed in particular as a capillary, such a strong throttle action is produced that the intake of air by suction is reliably prevented at this point even without a non-return valve.

During the subsequent relaxation after actuation of the locking element 8 the fluid 2 in the pressure chamber 11 is put under pressure by the drive spring 7 moving the conveying tube 9 back upwards—i.e. by spring force—and is expelled through the expulsion nozzle 12 where it is nebulised, particularly into particles in the micron or nm range, preferably particles destined for the lungs measuring about 5 microns, which form a cloud or jet of aerosol 14, as indicated in FIG. 1. The conveying and nebulizing of the fluid 2 are thus carried out purely mechanically, in particular without propellant gas and without electricity.

A user can inhale the aerosol 14, while an air supply can be sucked into the mouthpiece 13 through at least one air supply opening 15.

The nebulizer 1 comprises an upper housing part 16 and an inner part 17 which is rotatable relative thereto, on which an in particular manually operable housing part 18 is releasably fixed, particularly fitted on, preferably by means of a retaining element 19. In order to insert and/or replace the container 3 the housing part 18 can be detached from the nebulizer 1.

By manually rotating the housing part 18 the inner part 17 can be rotated relative to the upper housing part 16, by means of which the drive spring 7 can be tensioned in the axial direction by means of a gear acting on the holder 6. During tensioning the container 3 is moved axially downwards until the container 3 assumes an end position as shown in FIG. 2 in the tensioned state. During the nebulizing process the container 3 is moved back into its original position by the drive spring 7. The container thus performs a stroke during the tensioning process and during the nebulizing process.

The housing part 18 preferably forms a cap-like lower housing part and fits around or over a lower free end portion of the container 3. As the drive spring 7 is tensioned the container 3 moves with its end portion (further) into the housing part 18 or towards the end face thereof, while an axially acting spring 20 arranged in the housing part 18 comes to bear on the base 21 of the container and pierces the container 3 or a base seal thereon with a piercing element 22 when the container makes contact with it for the first time, to allow air in.

The nebulizer 1 comprises a monitoring device 23 which counts the actuations of the nebulizer 1, preferably by detecting the rotation of the inner part 17 relative to the upper part 16 of the housing. The monitoring device 23 operates purely mechanically in the embodiment shown.

The construction and mode of operation of a proposed nebulizer 1 will now be described in more detail, referring to FIGS. 3 to 6, but emphasizing only the essential differences from the nebulizer 1 according to FIGS. 1 and 2. The remarks relating to FIGS. 1 and 2 thus apply accordingly.

Figure 3:
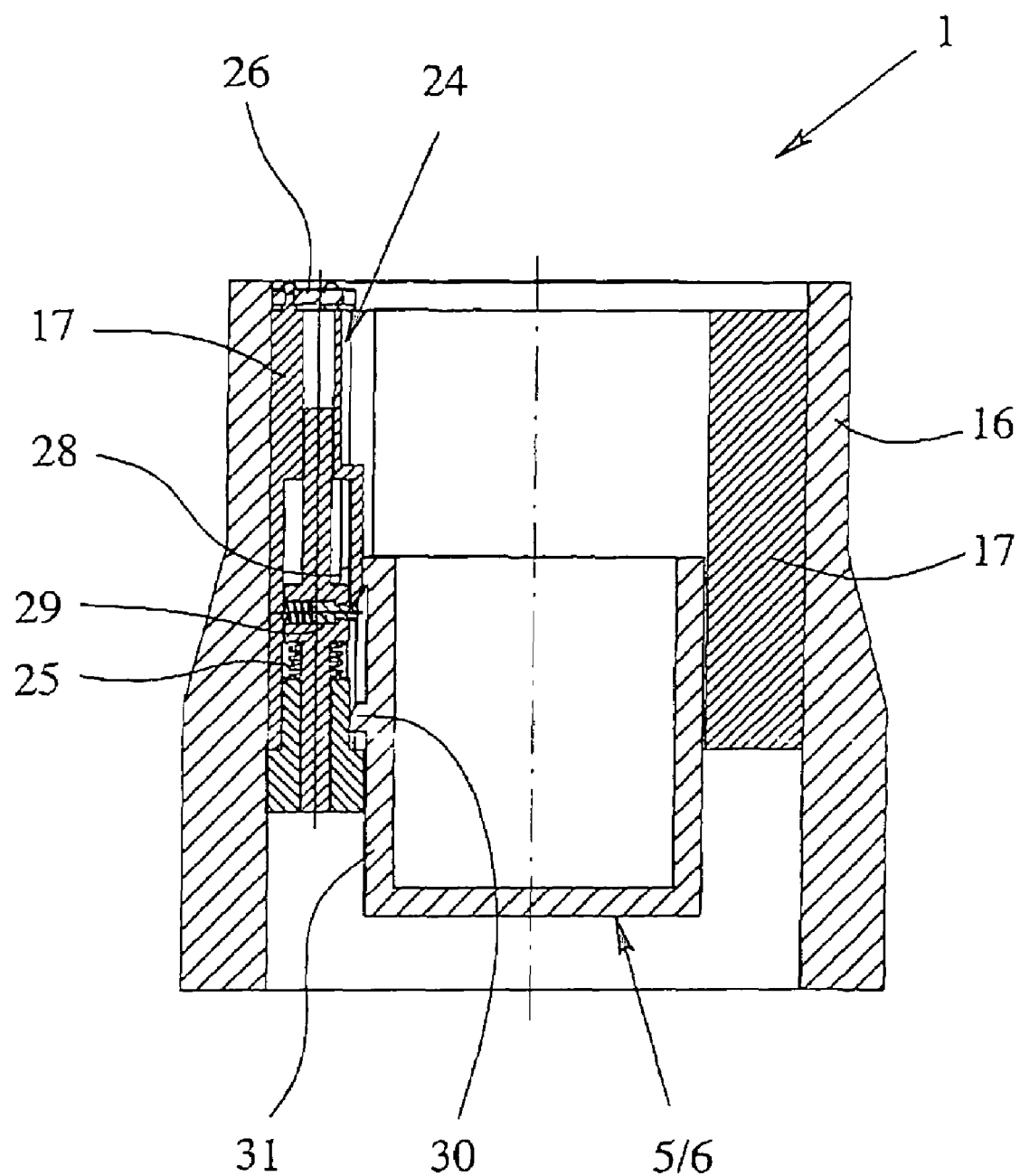
FIG. 3 is a diagrammatic sectional view of a detail of a proposed nebulizer according to a first embodiment with a signal device in the tensioned state.
Figure 4:
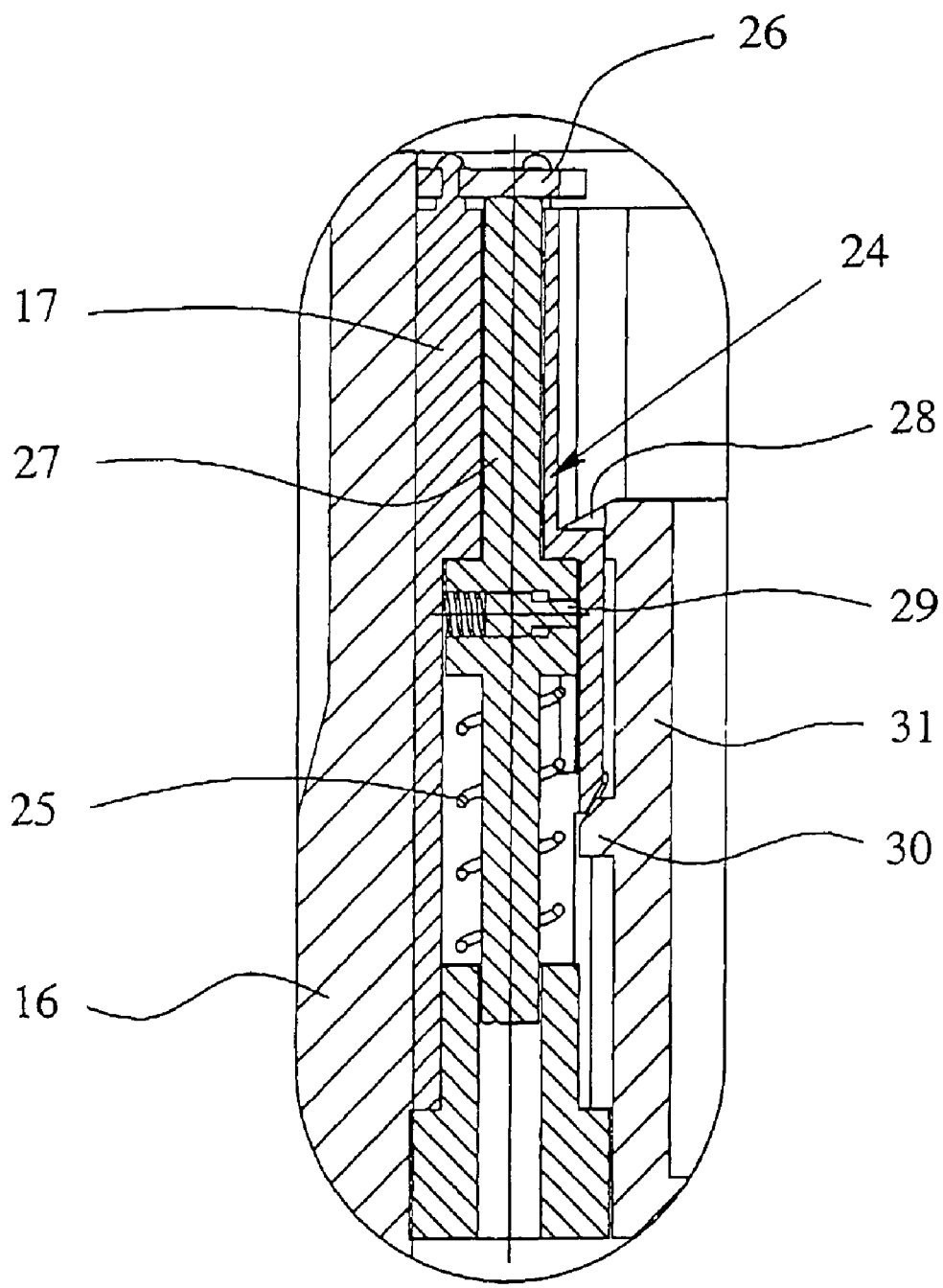
FIG. 4 is an enlarged view of a detail from FIG. 3 with the signal device untensioned.
Figure 5:
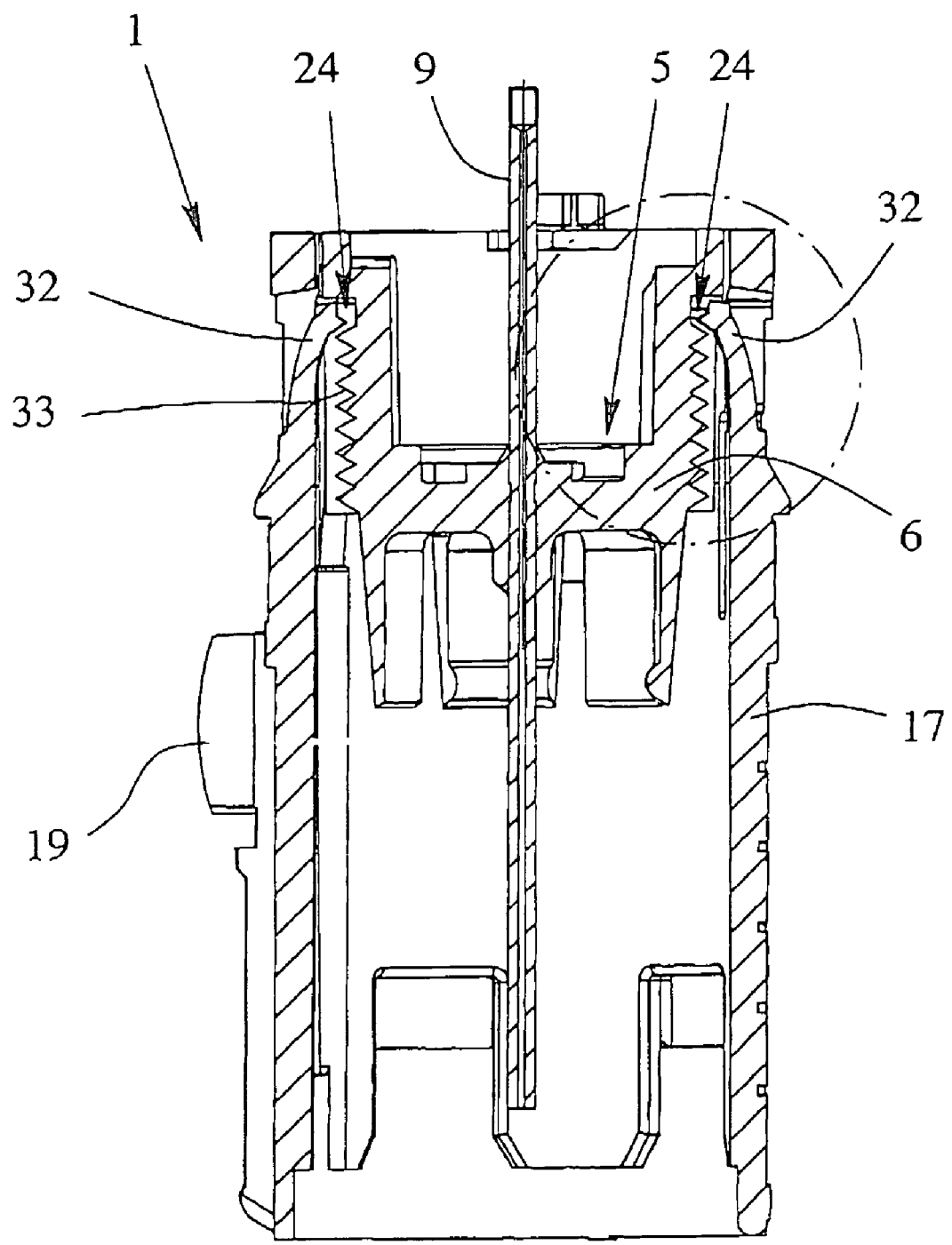
FIG. 5 is a diagrammatic sectional view of a detail of a proposed nebulizer according to a second embodiment with a signal device in the tensioned state.
Figure 6:
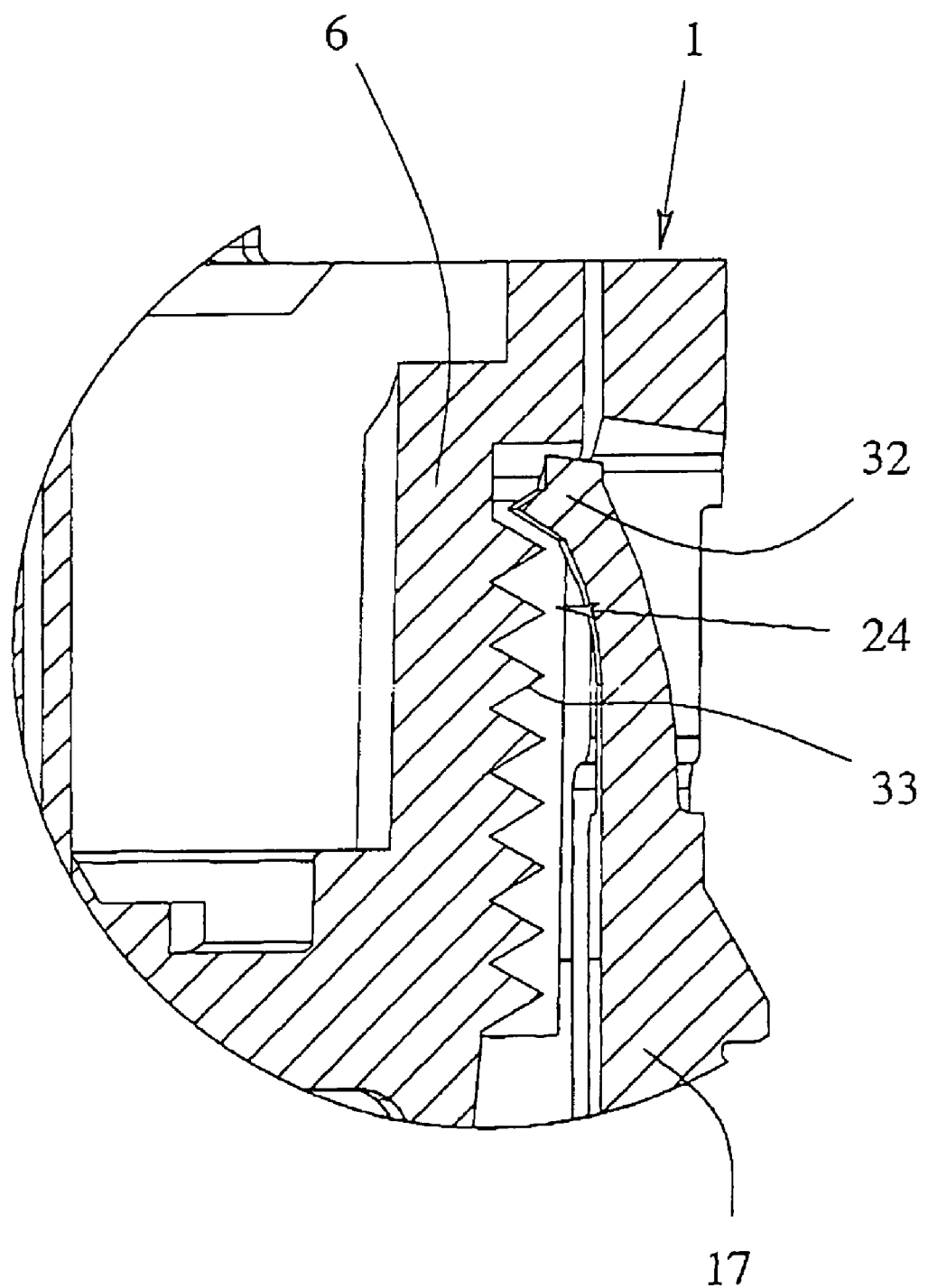
FIG. 6 is an enlarged view of a detail from FIG. 5.

FIG. 3 shows, in a highly diagrammatic sectional view of only certain details, a proposed nebulizer 1 according to a first embodiment with a signal device 24 for generating at least one acoustic and/or vibratory or otherwise tactile signal for guiding the user when using the nebulizer 1.

The signal device 24 preferably operates exclusively mechanical. Alternatively, however, the signal device 24 may also operate electrically or pneumatically, for example.

If necessary, the signal device 24 can be driven by the pressure generator 5, particularly the drive spring 7 thereof. However, the signal device 24 preferably comprises an energy store or drive particularly a spring store 25, independent of the pressure generator 5. In the embodiment shown, the spring store 25 is formed by a helical spring.

The signal device 24, particularly the spring store 25 thereof, can preferably be tensioned together with the pressure generator 5, particularly by a part such as the holder 6 of the pressure generator 5, particularly by rotating the housing part 18 and hence the inner part 17.

In the first embodiment the signal device 24 is preferably arranged in or on the inner part 17 which is rotatable, particularly for tensioning the nebulizer 1. However, the signal device 24 may also be mounted on or in some other suitable part of the nebulizer 1.

The signal device 24 comprises a preferably plate shaped impact element 26 and a tappet 27 or the like for actuating the impact element 26. Instead of the impact element 26 it is also possible to use any other suitable component for producing an acoustic and/or vibratory signal on striking the tappet 27.

The spring store 25 prestresses the tappet 27 towards the impact element 26. FIG. 3 shows the signal device 24 in the tensioned state; the tappet 27 is thus at a spacing from the impact element 26.

The tensioning of the tappet 27 counter to the force of the spring store 25 is preferably carried out in the embodiment shown together with the tensioning of the pressure generator 5. In particular, a tensioning cam 28 which is mounted on an axially moveable part of the pressure generator 5, particularly the holder 6 or a part connected therewith, engages on the tappet 27 as indicated in FIG. 3. The pressure generator 5 and the signal device 24 are thus preferably tensioned in the same direction.

In the tensioned state the tappet 27 can be located by means of a locking member 29 preferably in the form of a pin. The locking member 29 is preferably spring loaded and when the tensioned position is reached it automatically assumes its locking position as shown in FIG. 3.

The signal device 24 may be initiated or switched on by the pressure generator 5, particularly at the beginning and/or end of a nebulizing process.

In the embodiment shown the signal device 24 can only be initiated or switched on at the end of a nebulizing process. In particular, this is done by the pressure generator 5 shortly before or on reaching its untensioned state. In particular, a releasing cam 30 unlocks the signal device 24, as the releasing cam 30 meets the locking member 29 and presses it into a released position, so that the tappet 27 is moved and more particularly accelerated towards the impact element 26 by the force of the spring store 25 and strikes the impact element 26, producing the desired signal. The diagrammatic sectional view of a detail of the nebulizer 1 shown in FIG. 4 shows the signal device 24 in its relaxed state, i.e. during or after production of the signal.

Preferably, the tensioning cam 28 and the releasing cam 30 are arranged or formed on a common cam slide 31, as shown in FIG. 3.

Preferably, the cam slide 31 is moveable in order to tension the pressure generator 5 and during the nebulizing process.

In the first embodiment the signal device 24 generates a signal at the end of the nebulizing process in order to indicate to the user that the nebulizing process has ended. In particular, the signal device 24 is initiated or switched on by the pressure generator 5 at the end of a nebulizing process.

Alternatively or in addition, the signal device 24 may be initiated or switched on by the pressure generator 5 at the start of a nebulizing process. This is particularly advantageous when a signal is produced throughout the entire nebulizing process which indicates to the user that the nebulizing process is occurring. For example, this can be done by having the signal device 24 produce an airflow, e.g. by means of the tappet 27 or a piston, and this airflow in turn generates the desired signal, e.g. by means of a whistle or the like.

The signal device 24 can thus generate a signal additionally or alternatively throughout the duration of a nebulizing process.

According to an alternative embodiment, different signals can preferably be produced, e.g. to indicate the (ongoing) nebulizing process and to indicate the end of the nebulizing process.

If the signal device 24 can produce different signals, these preferably differ in their sound, duration, loudness, pitch or the like. According to an alternative embodiment, the signal device 24 is constructed so that acoustic or vibratory signals can be produced as required. This contributes to making the nebulizer 1 universally useable. If the signal device 24 can generate vibratory signals the nebulise 1 can be used or user more easily by those with hearing loss, in particular. Preferably, the signal generation can be switched off if desired and/or the user can choose whether to receive an acoustic signal, a vibratory signal or both types of signal from the signal device 24.

The nebulizing process usually lasts about 1 to 2 seconds. However, the inhalation process should be continued for about another 1 to 2 seconds in order that as much as possible of the nebulised fluid 2 or the cloud of aerosol 14 produced can be inhaled. Moreover, the user should hold the air in for about 5 to 15 seconds after breathing in or inhaling. For this reason, according to a particularly preferred embodiment, it is provided that the signal is only emitted after a certain delay after the end of the nebulizing process and/or a certain time after the end of the nebulizing. Preferably, therefore, the signal can be emitted during a predetermined time and/or after the predetermined time, particularly beginning with a nebulizing process, the time preferably being measured so that the user is informed of the recommended or required inhalation period of for example about 3 to 4 seconds or the recommended period of about 5 to 15 seconds of holding their breathe.

The above mentioned signal production may be carried out for example by initiating the signal device 24 only at the end of a nebulizing process—e.g. by the pressure generator 5—after which a signal is produced for a period of e.g. 1 to 15 seconds or only after 1 to 15 seconds. This can be achieved for example by producing an air current by means of the tappet 27 for directly generating a signal or for slowing down or attenuating the movement of the tappet towards the impact element 26.

Instead of a mechanical delay or a mechanical timer, if necessary an electronic timer can be used to produce the above mentioned delay or length of time to indicate the recommended or required inhalation process or the end thereof. In this case the signal device preferably works electrically or electronically.

According to another alternative embodiment the signal device 24 may also be adapted to be initiated independently of the pressure generator 5 or, for example, simultaneously by actuation of the locking element 8.

In a diagrammatic sectional view FIG. 5 shows a second embodiment of the proposed nebulizer with a different signal device 24. FIG. 6 shows an enlarged view of a detail from FIG. 5.

The signal device 24 comprises at least one ratchet element 32, in the embodiment shown two ratchet elements 32, which is or are moveable during a nebulizing process by means of a latch 33 to generate an acoustic signal. In particular, the relative movement of the latching means 33 to the ratchet elements 32 is carried out by the pressure generator 5 or its drive spring 7 during the nebulizing process.

Preferably, the latching means 33 are formed on the holder 6 or on a component connected thereto.

The ratchet elements 32 are preferably shaped like fingers and are particularly mounted or formed, preferably integrally formed, on the inner part 17 of the nebulizer 1.

The ratchet elements 32 are preferably elastically and particularly inherently elastically biased against the latching means 33.

In the second embodiment, the signal device 24 can emit an acoustic and/or vibratory signal during a nebulizing process as a result of the ratchet elements 32 moving over the latching means 33.

The latching means 33 may be formed by a thread so that when the latching means 33 are rotated relative to the ratchet elements 32 during the tensioning process the production of a signal can be avoided. Alternatively, the emitting of a signal during the tensioning process can also be prevented by other means or some other constructional solution.

The embodiments described above and particularly individual elements and aspects of the embodiments may if required be combined with one another and/or kinematically reversed.

We claim:

1. A nebulizer, comprising a pressure generator means for conveying and nebulizing a fluid and a signal device having means for generating at least one acoustic or vibratory signal for user guidance as to performance of an individual nebulizing process; wherein the signal device comprises different parts of the nebulizer from those which form the pressure generator means and wherein said means for generating at least one acoustic or vibratory signal comprises at least one element which produces said at least one acoustic or vibratory signal, in addition to any sound or vibration produced by the pressure generator means, by movement in a lengthwise direction of the nebulizer.

2. The nebulizer according to claim 1, further comprising a pressure generator adapted for triggering operation of the signal device.

3. A nebulizer for nebulizing a fluid, comprising a pressure generator means for conveying and nebulizing a fluid and a signal device having means for generating at least one acoustic or vibratory signal for user guidance, wherein the signal device comprises an energy store or drive independent of the pressure generator means, the signal device being formed of different parts of the nebulizer from those which form the pressure generator means, and wherein the signal device produces said acoustic or vibratory signal in addition to any sound or vibration produced by the pressure generator means.

4. The nebulizer according to claim 1, characterised in that the signal device is a mechanically operating signal device.

5. The nebulizer according to claim 1, characterised in that the signal device has an energy store comprising a spring store.

6. The nebulizer according to claim 5, characterised in that the spring store can be manually tensioned by a holder of a pressure generator for a container with a fluid to be nebulized.

7. The nebulizer according to claim 1, characterised in that the signal device comprises a substantially flat impact element which can be actuated in order to generate the signal.

8. The nebulizer according to claim 5, characterised in that the signal device comprises a tappet that can be actuated in order to generate the signal, and in that the tappet can be moved towards an impact element by the spring store in order to generate the signal.

9. The nebulizer according to claim 8, further comprising a tensioning cam which tensions the tappet counter to the force of the spring store.

10. The nebulizer according to one of claims 9, further comprising a locking means for locking that the tappet in the tensioned state.

11. The nebulizer according to claim 10, further comprising a pressure generator adapted for triggering operation of the signal device, wherein the tappet can be released by the pressure generator by means of a releasing cam.

12. The nebulizer according to claims 11, characterised in that the tensioning cam and the releasing cam are formed on a common cam slide.

13. The nebulizer according to claim 12, characterised in that the cam slide is moveable for tensioning the pressure generator and during the nebulizing process.

14. The nebulizer according to claim 3, wherein the signal device is a mechanically operating signal device.

15. The nebulizer according to claim 3, wherein the signal device has an energy store comprising a spring store.

16. The nebulizer according to claim 15, further comprising a holder of a pressure generator for a container with a fluid to be nebulized, wherein the spring store can be manually tensioned by the holder.

17. The nebulizer according to claim 15, wherein the signal device comprises a substantially flat impact element which is actuatable for generating the signal.

18. The nebulizer according to claim 15, wherein the signal device comprises a tappet that can be actuated for generating the signal, and wherein the tappet is movable towards an impact element by the spring store to generate the signal.

19. The nebulizer according to claim 18, further comprising a tensioning cam which tensions the tappet counter to the force of the spring store.

20. The nebulizer according to claim 19, further comprising a locking means for locking that the tappet in the tensioned state.

21. The nebulizer according to claim 20, wherein the pressure generator is adapted for triggering operation of the signal device, wherein the tappet can be released by the pressure generator by means of a releasing cam.

22. The nebulizer according to claim 21, wherein the tensioning cam and the releasing cam are formed on a common cam slide.

23. The nebulizer according to claim 22, wherein the cam slide is moveable for tensioning the pressure generator and during the nebulizing process.

24. The nebulizer according to claim 3, wherein the pressure generator is adapted for triggering operation of the signal device.

25. The nebulizer according to claim 3, wherein the signal device is a mechanically operating signal device.

26. The nebulizer according to claim 3, wherein the signal device has an energy store comprising a spring store.

27. The nebulizer according to claim 26, further comprising a holder of a pressure generator for a container with a fluid to be nebulized, wherein the spring store can be manually tensioned by the holder.

28. The nebulizer according to claim 3, wherein the signal device comprises a substantially flat impact element which is actuatable for generating the signal.

29. The nebulizer according to claim 26, wherein the signal device comprises a tappet that can be actuated for generating the signal, and wherein the tappet is movable towards an impact element by the spring store to generate the signal.

30. The nebulizer according to claim 29, further comprising a tensioning cam which tensions the tappet counter to the force of the spring store.

31. The nebulizer according to claim 30, further comprising a locking means for locking that the tappet in the tensioned state.

32. The nebulizer according to claim 31, wherein the pressure generator is adapted for triggering operation of the signal device, wherein the tappet can be released by the pressure generator by means of a releasing cam.

33. The nebulizer according to claim 32, wherein the tensioning cam and the releasing cam are formed on a common cam slide.

34. The nebulizer according to claim 33, wherein the cam slide is moveable for tensioning the pressure generator and during the nebulizing process.

35. The nebulizer according to claim 1, wherein the signal device comprises an energy store or drive.

* * * * *